(12) United States Patent
Nishino et al.

(10) Patent No.: US 7,358,394 B2
(45) Date of Patent: Apr. 15, 2008

(54) PROCESS FOR PREPARING N,N'-DIALKOXY-N, N'-DIALKYL OXAMIDE

(75) Inventors: Shigeyoshi Nishino, Ube (JP); Shoji Shikita, Ube (JP); Yoji Omata, Ube (JP)

(73) Assignee: Ube Industries, Ltd., Ube-shi (JP)

( * ) Notice: Subject to any disclaimer, the term of this patent is extended or adjusted under 35 U.S.C. 154(b) by 0 days.

(21) Appl. No.: 10/570,996

(22) PCT Filed: Sep. 9, 2004

(86) PCT No.: PCT/JP2004/013136

§ 371 (c)(1),
(2), (4) Date: Dec. 26, 2006

(87) PCT Pub. No.: WO2005/026108

PCT Pub. Date: Mar. 24, 2005

(65) Prior Publication Data

US 2007/0093675 A1    Apr. 26, 2007

(30) Foreign Application Priority Data

Sep. 9, 2003  (JP) ............................. 2003-316377
Jul. 26, 2004  (JP) ............................. 2004-217301

(51) Int. Cl.
*C07C 233/05* (2006.01)
(52) U.S. Cl. ..................... 564/152; 564/159
(58) Field of Classification Search ................ 564/152, 564/159
See application file for complete search history.

(56) References Cited

U.S. PATENT DOCUMENTS 6,265,434 B1   7/2001   Caldwell et al.

FOREIGN PATENT DOCUMENTS

JP   2002-541104 A   12/2002

WO   WO-00/59503 A1   10/2000

OTHER PUBLICATIONS

Edited by CSJ: The Chemical Society of Japan, "Shin Jikken Kagaku Kosa 14 Yuki Kagobutsu no Gosei to Han'no II", Maruzen Co., Ltd., Dec. 20, 1977, pp. 1226-1229.

*Primary Examiner*—Shailendra Kumar
(74) *Attorney, Agent, or Firm*—Birch, Stewart, Kolasch & Birch, LLP

(57) ABSTRACT

The present invention provides a process for preparing an N,N'-dialkoxy-N,N'-dialkyl oxamide represented by the formula (3):

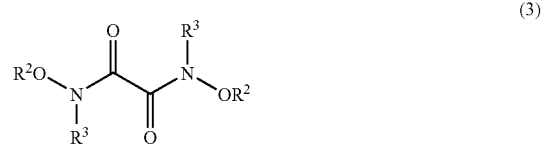

(3)

wherein $R^2$ and $R^3$ may be the same or different from each other, and each represent an alkyl group having 1 to 4 carbon atoms, which comprises reacting an oxalic acid diester represented by the formula (1):

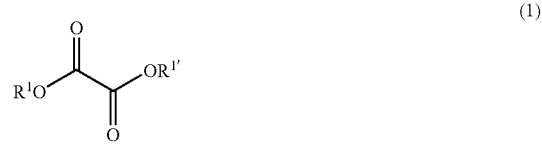

(1)

wherein $R^1$ and $R^{1'}$ may be the same or different from each other, and each represent a hydrocarbon group, and an N-alkyl-O-alkylhydroxylamine represented by the formula (2):

$$R^2O-NHR^3 \quad (2)$$

wherein $R^2$ and $R^3$ have the same meanings as defined above, or an acid salt thereof in the presence of a base.

16 Claims, No Drawings

PROCESS FOR PREPARING N,N'-DIALKOXY-N, N'-DIALKYL OXAMIDE

This application is a 371 of PCT/JP04/13136, filed Sep. 9, 2004.

TECHNICAL FIELD

The present invention relates to a novel process for preparing an N,N'-dialkoxy-N,N'-dialkyl oxamide which is useful as a synthetic intermediate for medicines, agricultural chemicals, etc.

BACKGROUND ART

Heretofore, as a method for preparing an N,N'-dialkoxy-N,N'-dialkyl oxamide, there has been disclosed a process in which oxalyl chloride and N,O-dimethylhydroxylamine hydrochloride are reacted in the presence of pyridine to prepare N,N'-dimethoxy-N,N'-dimethyl oxamide (for example, see J. Org. Chem., 60, 5016 (1995)). In this method, however, there are problems that phosgene having high toxicity and oxalyl chloride which is likely decomposed to carbon monoxide are used as starting materials, and yet methylene chloride having high carcinogenic properties must be used in an isolating operation of the objective product, so that it was not suitable for an industrial process for preparing an N,N'-dialkoxy-N,N'-dialkyl oxamide.

DISCLOSURE OF THE INVENTION

An object of the present invention is to solve the above-mentioned problems, and to provide an industrially suitable process for preparing an N,N'-dialkoxy-N,N'-dialkyl oxamide which uses safe starting materials, requires no complicated operation, and can prepare an N,N'-dialkoxy-N,N'-dialkyl oxamide in high yield.

The present invention relates to a process for preparing an N,N'-dialkoxy-N,N'-dialkyl oxamide represented by the formula (3):

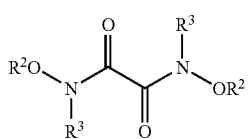

(3)

wherein $R^2$ and $R^3$ may be the same or different from each other, and each represent an alkyl group having 1 to 4 carbon atoms, which comprises reacting an oxalic acid diester represented by the formula (1):

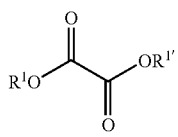

(1)

wherein $R^1$ and $R^{1'}$ may be the same or different from each other, and each represent a hydrocarbon group, and an N-alkyl-O-alkylhydroxylamine represented by the formula (2):

(2)

wherein $R^2$ and $R^3$ have the same meanings as defined above, or an acid salt thereof in the presence of a base.

BEST MODE FOR CARRYING OUT THE INVENTION

The oxalic acid diester to be used in the reaction of the present invention is represented by the above-mentioned formula (1). In the formula (1), $R^1$ and $R^{1'}$ may be the same or different from each other, and each represent a hydrocarbon group including, for example, an alkyl group having 1 to 8 carbon atoms such as a methyl group, an ethyl group, a propyl group, a butyl group, a pentyl group, a hexyl group, a heptyl group, an octyl group, etc.; a cycloalkyl group such as a cyclopropyl group, a cyclobutyl group, a cyclopentyl group, a cyclohexyl group, etc.; an aralkyl group such as a benzyl group, a phenethyl group, etc.; an aryl group such as a phenyl group, a tolyl group, a naphthyl group, etc. Of these, a methyl group, an ethyl group, an isopropyl group, a butyl group or a phenyl group is preferred. Incidentally, these groups also include various kinds of isomers.

The N-alkyl-O-alkylhydroxylamine to be used in the reaction of the present invention is represented by the above-mentioned formula (2). In the formula (2), $R^2$ and $R^3$ each may be the same or different from each other, and each represent an alkyl group having 1 to 4 carbon atoms including, for example, a methyl group, an ethyl group, a propyl group or a butyl group. Incidentally, these groups also include various kinds of isomers. Incidentally, said N-alkyl-O-alkylhydroxylamine may be used not only as a free N-alkyl-O-alkylhydroxylamine (including a hydrate thereof), but also as an acidic salt such as a hydrochloride, sulfate, nitrate, phosphate, etc., and it may be used as an aqueous solution thereof. Incidentally, these N-alkyl-O-alkylhydroxylamines may be used alone or in combination of two or more in admixture.

An amount of the above-mentioned N-alkyl-O-alkylhydroxylamine or an acid salt thereof is preferably 0.5 to 5.0 mols, more preferably 1.5 to 3.0 mols based on 1 mol of the oxalic acid diester.

As the base to be used in the reaction of the present invention, there may be mentioned, for example, an alkali metal alkoxide (containing a corresponding alcohol solution thereof) such as lithium methoxide, sodium methoxide, sodium ethoxide, potassium methoxide, potassium ethoxide, potassium t-butoxide, etc.; an alkali metal hydroxide such as sodium hydroxide, potassium hydroxide, etc.; an alkali metal carbonate such as lithium carbonate, sodium carbonate, potassium carbonate, etc.; an alkali metal hydrogen carbonate such as sodium hydrogen carbonate, potassium hydrogen carbonate, etc.; an amine such as triethylamine, tributylamine, etc., preferably an alkali metal alkoxide, more preferably sodium methoxide, sodium ethoxide is/are used. Incidentally, these bases may be used alone or in combination of two or more in admixture.

An amount of the above-mentioned base to be used is preferably 0.5 to 10 mols, more preferably 1.5 to 6 mols based on 1 mol of the oxalic acid diester.

The reaction of the present invention is preferably carried out in a solvent. As the solvent to be used, it is not particularly limited so long as it does not interfere the reaction, and there may be mentioned, for example, an alcohol such as methanol, ethanol, n-propyl alcohol, isopropyl alcohol, n-butyl alcohol, sec-butyl alcohol, t-butyl alcohol, etc.; a nitrile such as acetonitrile, propionitrile, etc.; an aliphatic hydrocarbon such as hexane, heptane, etc.; a halogenated aliphatic hydrocarbon such as methylene chloride, chloroform, carbon tetrachloride ide, etc.; an aromatic hydrocarbon such as benzene, toluene, xylene, mesitylene, etc.; a halogenated aromatic hydrocarbon such as chlorobenzene, etc.; an ether such as diethyl ether, tetrahydrofuran, diisopropyl ether, dioxane, etc.; an amide such as N,N-dimethylformamide, N,N-dimethyl-acetamide, etc.; a carboxylic acid ester such as ethyl acetate, butyl acetate, ethyl propionate, etc.; a sulfoxide such as dimethylsulfoxide, etc.; a carbonic acid diester such as dimethyl carbonate, diethyl carbonate, etc., preferably an alcohol, a nitrile, an aromatic hydrocarbon, more preferably methanol, ethanol, isopropyl alcohol is/are used. Incidentally, these solvents may be used alone or in combination of two or more in admixture.

An amount of the above-mentioned solvent to be used may be optionally adjusted depending on a degree of uniformity or condition of stirring of the reaction solution, and is preferably 0.1 to 100 g, more preferably 0.5 to 50 g based on 1 g of the oxalic acid diester.

The reaction of the present invention can be carried out, for example, by mixing an oxalic acid diester, an N-alkyl-O-alkylhydroxylamine or an acid salt thereof, a base and a solvent, and reacted under stirring, or the like. A reaction temperature at that time is preferably −40 to 100° C., more preferably −20 to 50° C., and a reaction pressure and a reaction time are not specifically limited.

As the N,N'-dialkoxy-N,N'-dialkyl oxamide to be obtained in the present invention, there may be mentioned, for example, a compound wherein $R^2$ and $R^3$ are each may be the same or different from each other, and each is an alkyl group having 1 to 4 carbon atoms.

Incidentally, the N,N'-dialkoxy-N,N'-dialkyl oxamide which is a final product can be isolated and purified by, for example, a general method such as filtration, concentration, distillation, recrystallization, column chromatography, etc., after completion of the reaction.

The N,N'-dialkoxy-N,N'-dialkyl oxamide obtained in the present invention, can be led to useful medicine or agricultural chemicals according to the methods as disclosed in, for example, Japanese PCT Patent Publication 2002-541104, Japanese PCT Patent Publication 2004-509059 or Bioorganic and Medicinal Chemistry Letters (Bioorg. Med. Chem. Lett. 12 (2002) pp. 3001-3004), etc.

Next, the present invention will be explained more specifically by referring to Examples, but the scope of the present invention is not limited by these.

EXAMPLES

Example 1

Synthesis of N,N'-dimethoxy-N,N'-dimethyl oxamide

In a flask having an inner volume of 1000 ml and equipped with a stirring device, a thermometer and a dropping funnel were charged 126.8 g (0.85 mol) of 98% by weight diethyl oxalate, 169.0 g (1.70 mol) of 98.1% by weight N,O-dimethylhydroxylamine hydrochloride and 100 ml of methanol, and while maintaining the liquid temperature to 5 to 10° C., 656.0 g (3.40 mol) of 28% by weight sodium methoxide-methanol solution was gradually added dropwise to the mixture, and then reacted at the same temperature for 3 hours under stirring. After completion of the reaction, in a flask having an inner volume of 2000 ml and equipped with a stirring device, a thermometer and a dropping funnel were charged 107.1 g (1.79 mol) of acetic acid and 893 g of water and the mixture was cooled to 5° C. Then, the above-mentioned reaction mixture was gradually added dropwise to the mixture while maintaining the liquid temperature to 5 to 15° C., and the resulting mixture was stirred. Then, the reaction mixture was concentrated under reduced pressure, and the concentrate was extracted with 1500 ml of ethyl acetate. The obtained organic layer (ethyl acetate layer) was again concentrated under reduced pressure, 240 g of n-heptane was added to the residue, and the mixture was stirred for 30 minutes while the liquid temperature was maintained to 5 to 10° C. The precipitated crystals were collected by filtration, washed with cooled n-heptane and dried under reduced pressure to give 92.3 g (Isolation yield: 61.6%) of N,N'-dimethoxy-N,N'-dimethyl oxamide as white crystal.

Incidentally, physical properties of the N,N'-dimethoxy-N,N'-dimethyl oxamide were as follows.

Melting point; 89.5 to 92.0° C. $^1$H-NMR (CDCl$_3$, δ (ppm)); 3.24 (6H, s), 3.74 (6H, s)

Example 2

Synthesis of N,N'-dimethoxy-N,N'-dimethyl oxamide

In a flask having an inner volume of 25 ml and equipped with a stirring device, a thermometer and a dropping funnel were charged 1.01 g (8.47 mmol) of 99% by weight dimethyl oxalate, 1.68 g (16.94 mmol) of 98.1% by weight N,O-dimethylhydroxylamine hydrochloride and 1 ml of methanol, and while maintaining the liquid temperature to 5 to 10° C., 6.54 g (33.88 mmol) of a 28% by weight sodium methoxide-methanol solution was gradually added dropwise, and the mixture was reacted at the same temperature for 3 hours under stirring. After completion of the reaction, in a flask having an inner volume of 25 ml and equipped with a stirring device, a thermometer and a dropping funnel was charged 10 ml (2.00 mmol) of 2 mol/l acetic acid and the liquid was cooled to 5° C. Then, the above-mentioned reaction mixture was gradually added dropwise to the liquid while maintaining the liquid temperature to 5 to 15° C., and the resulting mixture was stirred. When this solution was analyzed (the absolute quantitative method) by high performance liquid chromatography, 1.21 g (Reaction yield: 80.9%) of N,N'-dimethoxy-N,N'-dimethyl oxamide was found to be formed.

Example 3

Synthesis of N,N'-dimethoxy-N,N'-dimethyl oxamide

The reaction was carried out in the same manner as in Example 2 except for changing 1.01 g (8.47 mmol) of 99% by weight dimethyl oxalate to 1.26 g (8.47 mmol) of 98% by weight diethyl oxalate, and changing methanol to ethanol in Example 2. As a result, 1.29 g (Reaction yield: 86.4%) of N,N'-dimethoxy-N,N'-dimethyl oxamide was found to be formed.

Example 4

Synthesis of N,N'-dimethoxy-N,N'-dimethyl oxamide

The reaction was carried out in the same manner as in Example 2 except for changing 1.01 g (8.47 mmol) of 99% by weight dimethyl oxalate to 1.49 g (8.47 mmol) of 99% by weight diisopropyl oxalate, and changing methanol to ethanol in Example 2. As a result, 1.23 g (Reaction yield: 82.4%) of N,N'-dimethoxy-N,N'-dimethyl oxamide was found to be formed.

Example 5

Synthesis of N,N'-dimethoxy-N,N'-dimethyl oxamide

The reaction was carried out in the same manner as in Example 2 except for changing 1.01 g (8.47 mmol) of 99% by weight dimethyl oxalate to 1.73 g (8.47 mmol) of 99% by weight dibutyl oxalate, and changing methanol to ethanol in Example 2. As a result, 1.24 g (Reaction yield: 83.1%) of N,N'-dimethoxy-N,N'-dimethyl oxamide was found to be formed.

Example 6

Synthesis of N,N'-dimethoxy-N,N'-dimethyl oxamide

The reaction was carried out in the same manner as in Example 2 except for changing 1.01 g (8.47 mmol) of 99% by weight dimethyl oxalate to 2.07 g (8.47 mmol) of 99% by weight diphenyl oxalate, and changing methanol to ethanol in Example 2. As a result, 0.85 g (Reaction yield: 57.1%) of N,N'-dimethoxy-N,N'-dimethyl oxamide was found to be formed.

Example 7

Synthesis of N,N'-dimethoxy-N,N'-dimethyl oxamide

The reaction was carried out in the same manner as in Example 3 except for changing ethanol to isopropyl alcohol in Example 3. As a result, 1.21 g (Reaction yield: 80.8%) of N,N'-dimethoxy-N,N'-dimethyl oxamide was found to be formed.

Example 8

Synthesis of N,N'-dimethoxy-N,N'-dimethyl oxamide

The reaction was carried out in the same manner as in Example 3 except for changing ethanol to acetonitrile in Example 3. As a result, 1.18 g (Reaction yield: 78.8%) of N,N'-dimethoxy-N,N'-dimethyl oxamide was found to be formed.

Example 9

Synthesis of N,N'-dimethoxy-N,N'-dimethyl oxamide

The reaction was carried out in the same manner as in Example 3 except for changing ethanol to dimethylcarbonate in Example 3. As a result, 1.13 g (Reaction yield: 75.7%) of N,N'-dimethoxy-N,N'-dimethyl oxamide was found to be formed.

Example 10

Synthesis of N,N'-dimethoxy-N,N'-dimethyl oxamide

The reaction was carried out in the same manner as in Example 3 except for changing ethanol to dimethylformamide in Example 3. As a result, 1.16 g (Reaction yield: 77.5%) of N,N'-dimethoxy-N,N'-dimethyl oxamide was found to be formed.

Example 11

Synthesis of N,N'-dimethoxy-N,N'-dimethyl oxamide

The reaction was carried out in the same manner as in Example 3 except for changing ethanol to tetrahydrofuran in Example 3. As a result, 1.25 g (Reaction yield: 83.6%) of N,N'-dimethoxy-N,N'-dimethyl oxamide was found to be formed.

Example 12

Synthesis of N,N'-dimethoxy-N,N'-dimethyl oxamide

The reaction was carried out in the same manner as in Example 3 except for changing ethanol to toluene in Example 3. As a result, 1.05 g (Reaction yield: 71.0%) of N,N'-dimethoxy-N,N'-dimethyl oxamide was found to be formed.

Example 13

Synthesis of N,N'-dimethoxy-N,N'-dimethyl oxamide

In a flask having an inner volume of 25 ml and equipped with a stirring device and a thermometer were charged 1.01 g (8.47 mmol) of 99% by weight dimethyl oxalate, 1.68 g (16.94 mmol) of 98.1% by weight N,O-dimethylhydroxylamine hydrochloride and 5 ml of dimethyl-sulfoxide, and while maintaining the liquid temperature to 5 to 25° C., 1.93 g (33.88 mmol) of 95% by weight sodium methoxide powder was charged to the mixture by dividing the powder to several portions, and the resulting mixture was reacted at the same temperature for 1.5 hours under stirring. After completion of the reaction, in a flask having an inner volume of 25 ml and equipped with a stirring device, a thermometer and a dropping funnel was charged 10 ml (2.00 mmol) of 2 mol/l acetic acid and the liquid was cooled to 5° C. Then, the above-mentioned reaction mixture was gradually added dropwise to the liquid while maintaining the liquid temperature to 5 to 15° C., and the resulting mixture was stirred. When this solution was analyzed (the absolute quantitative method) by high performance liquid chromatography, 0.91 g (Reaction yield: 61.0%) of N,N'-dimethoxy-N,N'-dimethyl oxamide was found to be formed.

Example 14

Synthesis of N,N'-dimethoxy-N,N'-dimethyl oxamide

In a flask having an inner volume of 200 ml and equipped with a stirring device, a thermometer and a dropping funnel were charged 12.63 g (84.7 mmol) of 98% by weight diethyl oxalate, 16.72 g (169.4 mmol) of 98.8% by weight N,O-dimethylhydroxylamine hydrochloride and 10 ml of methanol, and while maintaining the liquid temperature to 3 to 7° C., 65.36 g (338.8 mmol) of 28% by weight sodium methoxide-methanol solution was gradually added dropwise, and the resulting mixture was reacted at 3 to 8° C. for 3 hours under stirring. After completion of the reaction, in a flask having an inner volume of 300 ml and equipped with a stirring device, a thermometer and a dropping funnel was charged 90 ml (180 mmol) of 2 mol/l hydrochloric acid and the liquid was cooled to 5° C. Then, the above-mentioned reaction mixture was gradually added dropwise to the liquid while maintaining the liquid temperature to 5 to 15° C., and the resulting mixture was stirred. When this solution was analyzed (the absolute quantitative method) by high performance liquid chromatography, 13.25 g (Reaction yield: 88.8%) of N,N'-dimethoxy-N,N'-dimethyl oxamide was found to be formed.

Example 15

Synthesis of N,N'-dimethoxy-N,N'-dimethyl oxamide

In a flask having an inner volume of 200 ml and equipped with a stirring device, a thermometer and a dropping funnel were charged 12.63 g (84.7 mmol) of 98% by weight diethyl oxalate, 16.72 g (169.4 mmol) of 98.8% by weight N,O-dimethylhydroxylamine hydrochloride and 10 ml of methanol, and while maintaining the liquid temperature to −10 to −7° C., 65.36 g (338.8 mmol) of 28% by weight sodium methoxide-methanol solution was gradually added dropwise to the mixture, and the resulting mixture was reacted at −9 to −7° C. for 3 hours under stirring. After completion of the reaction, in a flask having an inner volume of 300 ml and equipped with a stirring device, a thermometer and a dropping funnel was charged 90 ml (180 mmol) of 2 mol/l hydrochloric acid and the liquid was cooled to 5° C. Then, while maintaining the liquid temperature to 5 to 15° C., the above-mentioned reaction mixture was gradually added dropwise to the liquid and the resulting mixture was stirred. When this solution was analyzed (the absolute quantitative method) by high performance liquid chromatography, 13.12 g (Reaction yield: 87.9%) of N,N'-dimethoxy-N,N'-dimethyl oxamide was found to be formed.

Example 16

Synthesis of N,N'-dimethoxy-N,N'-dimethyl oxamide

In a flask having an inner volume of 200 ml and equipped with a stirring device, a thermometer and a dropping funnel were charged, 12.63 g (84.7 mmol) of 98% by weight diethyl oxalate, 20.07 g (203.3 mmol) of 98.8% by weight N,O-dimethylhydroxylamine hydrochloride and 10 ml of methanol, and while maintaining the liquid temperature to 3 to 7° C., 71.90 g (372.7 mmol) of 28% by weight sodium methoxide-methanol solution was gradually added dropwise to the mixture, and the resulting mixture was reacted at 3 to 7° C. for 3 hours under stirring. After completion of the reaction, in a flask having an inner volume of 300 ml and equipped with a stirring device, a thermometer and a dropping funnel was charged 110 ml (187 mmol) of 1.7 mol/l hydrochloric acid and the liquid was cooled to 5° C. Then, while maintaining the liquid temperature to 5 to 15° C., the above-mentioned reaction mixture was gradually added dropwise to the liquid and the resulting mixture was stirred. When this solution was analyzed (the absolute quantitative method) by high performance liquid chromatography, 14.32 g (Reaction yield: 96.0%) of N,N'-dimethoxy-N,N'-dimethyl oxamide was found to be formed.

UTILIZABLE FIELD IN INDUSTRY

The present invention relates to a novel process for preparing an N,N'-dialkoxy-N,N'-dialkyl oxamide which is useful as a synthetic intermediate of medicines, agricultural chemicals, etc.

According to the present invention, an industrially suitable process for preparing an N,N'-dialkoxy-N,N'-dialkyl oxamide which uses safe starting materials, requires no complicated operation, and can prepare an N,N'-dialkoxy-N,N'-dialkyl oxamide in high yield can be provided.

What is claimed is:

1. A process for preparing an N,N'-dialkoxy-N,N'-dialkyl oxamide represented by the formula (3):

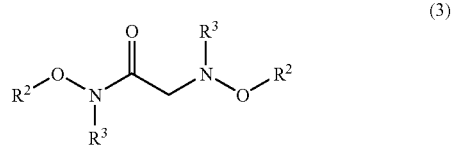

wherein $R^2$ and $R^3$ may be the same or different from each other, and each represent an alkyl group having 1 to 4 carbon atoms, which comprises reacting an oxalic acid diester represented by the formula (1):

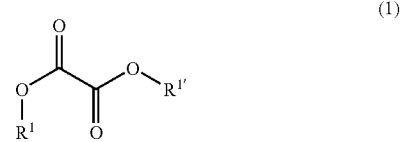

wherein $R^1$ and $R^{1'}$ may be the same or different from each other, and each represent a hydrocarbon group, and an N-alkyl-O-alkylhydroxylamine represented by the formula (2):

$$R^2O-NHR^3 \quad (2)$$

wherein $R^2$ and $R^3$ have the same meanings as defined above, or an acid salt thereof in the presence of a base.

2. The process for preparing an N,N'-dialkoxy-N,N'-dialkyl oxamide according to claim 1, wherein the base is at least one selected from the group consisting of an alkali metal alkoxide, an alkali metal hydroxide, an alkali metal carbonate, an alkali metal hydrogen carbonate and an amine.

3. The process for preparing an N,N'-dialkoxy-N,N'-dialkyl oxamide according to claim 1, wherein the base is at least one selected from the group consisting of lithium methoxide, sodium methoxide, sodium ethoxide, potassium methoxide, potassium ethoxide, potassium t-butoxide, sodium hydroxide, potassium hydroxide, lithium carbonate, sodium carbonate, potassium carbonate, sodium hydrogen carbonate, potassium hydrogen carbonate, triethylamine and tributylamine.

4. The process for preparing an N,N'-dialkoxy-N,N'-dialkyl oxamide according to claim 1, wherein the base is at least one selected from the group consisting of sodium methoxide and sodium ethoxide.

5. The process for preparing an N,N'-dialkoxy-N,N'-dialkyl oxamide according to claim 1, wherein the base is used in an amount of 0.5 to 10 mols based on 1 mol of the oxalic acid diester.

6. The process for preparing an N,N'-dialkoxy-N,N'-dialkyl oxamide according to claim 1, wherein the base is used in an amount of 1.5 to 6 mols based on 1 mol of the oxalic acid diester.

7. The process for preparing an N,N'-dialkoxy-N,N'-dialkyl oxamide according to claim 1, wherein the reaction is carried out in a solvent.

8. The process for preparing an N,N'-dialkoxy-N,N'-dialkyl oxamide according to claim 7, wherein the solvent is at least one selected from the group consisting of an alcohol; a nitrile; an aliphatic hydrocarbon; a halogenated aliphatic hydrocarbon; an aromatic hydrocarbon; a halogenated aromatic hydrocarbon; an ether; an amide; a carboxylic acid ester; a sulfoxide; and a carbonic acid diester.

9. The process for preparing an N,N'-dialkoxy-N,N'-dialkyl oxamide according to claim 7, wherein the solvent is at least one selected from the group consisting of methanol, ethanol, n-propyl alcohol, isopropyl alcohol, n-butyl alcohol, sec-butyl alcohol, t-butyl alcohol, acetonitrile, propionitrile, hexane, heptane, methylene chloride, chloroform, carbon tetrachloride, benzene, toluene, xylene, mesitylene, chlorobenzene, diethyl ether, tetrahydrofuran, diisopropyl ether, dioxane, N,N-dimethylformamide, N,N-dimethylacetamide, ethyl acetate, butyl acetate, ethyl propionate, dimethylsulfoxide, dimethyl carbonate and diethyl carbonate.

10. The process for preparing an N,N'-dialkoxy-N,N'-dialkyl oxamide according to claim 7, wherein the solvent is used in an amount of 0.1 to 100 g based on 1 g of the oxalic acid diester.

11. The process for preparing an N,N'-dialkoxy-N,N'-dialkyl oxamide according to claim 7, wherein the solvent is used in an amount of 0.5 to 50 g based on 1 g of the oxalic acid diester.

12. The process for preparing an N,N'-dialkoxy-N,N'-dialkyl oxamide according to claim 1, wherein $R^1$ and $R^{1'}$ of the oxalic acid diester represented by the formula (1) are each at least one selected from the group consisting of an alkyl group; a cycloalkyl group; an aralkyl group; and an aryl group.

13. The process for preparing an N,N'-dialkoxy-N,N'-dialkyl oxamide according to claim 1, wherein $R^1$ and $R^{1'}$ of the oxalic acid diester represented by the formula (1) are each at least one selected from the group consisting of a methyl group, an ethyl group, a propyl group, a butyl group, a pentyl group, a hexyl group, a heptyl group, an octyl group, a cyclopropyl group, a cyclobutyl group, a cyclopentyl group, a cyclohexyl group, a benzyl group, a phenethyl group, a phenyl group, a tolyl group and a naphthyl group.

14. The process for preparing an N,N'-dialkoxy-N,N'-dialkyl oxamide according to claim 1, wherein $R^2$ and $R^3$ of the N-alkyl-O-alkylhydroxylamine represented by the formula (2) are each at least one selected from the group consisting of a methyl group, an ethyl group, a propyl group and a butyl group.

15. The process for preparing an N,N'-dialkoxy-N,N'-dialkyl oxamide according to claim 1, wherein an amount of the N-alkyl-o-alkylhydroxylamine represented by the formula (2) or an acid salt thereof is 0.5 to 5.0 mols based on 1 mol of the oxalic acid diester represented by the formula (1).

16. The process for preparing an N,N'-dialkoxy-N,N'-dialkyl oxamide according to claim 1, wherein an amount of the N-alkyl-O-alkylhydroxylamine represented by the formula (2) or an acid salt thereof is 1.5 to 3.0 mols based on 1 mol of the oxalic acid diester represented by the formula (1).

* * * * *